US012558140B2

(12) United States Patent
Xiao et al.

(10) Patent No.: US 12,558,140 B2
(45) Date of Patent: Feb. 24, 2026

(54) CRYOGENIC BALLOON CATHETER HAVING HEATING FUNCTION

(71) Applicant: PIEDMONT MEDSYSTEMS (ZHUHAI) CO., LTD., Hengqin New Area (CN)

(72) Inventors: Jiahua Xiao, Hengqin New Area (CN); Enguang Li, Hengqin New Area (CN)

(73) Assignee: PIEDMONT MEDSYSTEMS (ZHUHAI) CO., LTD., Hengqin New Area (CN)

( * ) Notice: Subject to any disclaimer, the term of this patent is extended or adjusted under 35 U.S.C. 154(b) by 391 days.

(21) Appl. No.: 18/249,017

(22) PCT Filed: Oct. 15, 2021

(86) PCT No.: PCT/CN2021/124146
§ 371 (c)(1),
(2) Date: Apr. 13, 2023

(87) PCT Pub. No.: WO2022/078505
PCT Pub. Date: Apr. 21, 2022

(65) Prior Publication Data
US 2023/0397943 A1     Dec. 14, 2023

(30) Foreign Application Priority Data
Oct. 15, 2020     (CN) .......................... 202011106551.8

(51) Int. Cl.
*A61B 18/02* (2006.01)
*A61B 18/00* (2006.01)
(52) U.S. Cl.
CPC ...... *A61B 18/02* (2013.01); *A61B 2018/0022* (2013.01); *A61B 2018/00714* (2013.01);
(Continued)

(58) Field of Classification Search
CPC ............ A61B 18/02; A61B 2018/0022; A61B 2018/00714; A61B 2018/0212;
(Continued)

(56) References Cited

U.S. PATENT DOCUMENTS

| 5,899,897 A | 5/1999 | Rabin et al. |
| 5,906,612 A | 5/1999 | Chinn |

(Continued)

FOREIGN PATENT DOCUMENTS

| CN | 1440727 A | 9/2003 |
| CN | 106901827 A | 6/2017 |

(Continued)

OTHER PUBLICATIONS

Written Opinion of the International Searching Auhtority dated Jan. 17, 2022.
(Continued)

*Primary Examiner* — Ankit D Tejani
*Assistant Examiner* — Joshua Brendon Solomon
(74) *Attorney, Agent, or Firm* — Jacob M. Ward; Ward Law Office LLC

(57) ABSTRACT

A cryogenic balloon catheter having a heating function, the cryogenic balloon catheter comprising a catheter, an external power source, wherein an outer wall of the catheter comprises an inner layer, a middle layer and an outer layer, which are sequentially arranged from inside to outside, the middle layer comprising a metal woven mesh, and the metal woven mesh, the temperature controller and the external power source forming a power supply circuit. In the cryogenic balloon catheter, the middle layer of the outer wall of the cryogenic balloon catheter is provided with the metal woven mesh having a heat conduction function, and the metal woven mesh is connected to the external power source, such that the metal woven mesh can generate heat
(Continued)

after being powered, so as to ensure that the temperature of the outer surface of the catheter is maintained within set temperatures, thereby ensuring the cryogenic ablation effect.

12 Claims, 2 Drawing Sheets

(52) U.S. Cl.
CPC ................. *A61B 2018/0212* (2013.01); *A61B 2018/0237* (2013.01)

(58) Field of Classification Search
CPC .. A61B 2018/0237; A61B 2018/00041; A61B 2018/00791; A61B 2018/0262; A61B 2018/0293
See application file for complete search history.

(56) References Cited

U.S. PATENT DOCUMENTS

| | | | |
|---|---|---|---|
| 7,255,693 | B1 | 8/2007 | Johnston et al. |
| 2002/0156469 | A1 | 10/2002 | Yon et al. |
| 2007/0276360 | A1 | 11/2007 | Johnston et al. |
| 2008/0004534 | A1 | 1/2008 | Gelbart et al. |
| 2010/0268217 | A1 | 10/2010 | Habib |
| 2011/0178514 | A1 | 7/2011 | Levin et al. |
| 2012/0101413 | A1* | 4/2012 | Beetel ................ A61B 18/1492 601/3 |
| 2012/0289982 | A1 | 11/2012 | Gunday et al. |
| 2013/0123770 | A1 | 5/2013 | Smith |
| 2014/0316398 | A1 | 10/2014 | Kelly et al. |
| 2015/0018808 | A1 | 1/2015 | Mihalik |
| 2015/0038960 | A1 | 2/2015 | Gunday et al. |
| 2016/0206295 | A1 | 7/2016 | Kramer et al. |
| 2017/0189106 | A1* | 7/2017 | Schuler .................. A61B 18/02 |
| 2019/0159837 | A1* | 5/2019 | Park .................. A61M 25/0051 |

FOREIGN PATENT DOCUMENTS

| | | |
|---|---|---|
| CN | 208989115 U | 6/2019 |
| CN | 109965973 A | 7/2019 |
| CN | 112137712 A | 12/2020 |
| CN | 214231495 U | 9/2021 |
| JP | H04338472 A | 11/1992 |
| JP | H4338472 B2 | 10/2009 |
| WO | 03059247 A2 | 7/2003 |

OTHER PUBLICATIONS

International Search Report of the International application No. PCT/CN2021/124146 dated Jan. 17, 2022.
First Office Action dated Dec. 13, 2024 for Chinese patent application No. 202011106551.8.
Final Rejection dated Dec. 3, 2024 for Japanese patent application No. 2023-523140.
Second Office Action dated May 27, 2025 for CN patent application No. 202011106551.8.

* cited by examiner

CRYOGENIC BALLOON CATHETER HAVING HEATING FUNCTION

CROSS-REFERENCE TO RELATED APPLICATIONS

This patent application claims priority to International Patent Application No. PCT/CN2021/124146 filed on Oct. 15, 2021, which claims the benefit and priority of Chinese Patent Application 202011106551.8 filed with the China National Intellectual Property Administration on Oct. 15, 2020, the disclosures of which are incorporated herein by reference.

FIELD

The present application relates to the technical field of cryoablation devices, in particular to a cryogenic balloon catheter having a heating function.

BACKGROUND

In the medical industry, cryogenic balloon catheters for the interventional operation currently suffer from the following problems:

The catheter enters the body through the blood vessel of the human body, generally has an outer diameter of 3-4 mm, and has a thin wall in order to ensure adequate space for an inner diameter. When cryogenic fluid is introduced into the balloon catheter, cold will be transferred to the outer surface of the catheter from the inside of the catheter since the balloon catheter is less significant in thermal insulation effect due to the thin wall. When the temperature of the fluid introduced into the catheter is low enough (e.g., <−80° C.), there may have an impact on blood flowing on the outer surface of the catheter, and may even cause the phenomenon that blood vessels are frozen, and human tissues are damaged by freezing. This can endanger the life of the surgery patient.

Therefore, there is a need to design a cryogenic balloon catheter that can avoid damaging the human tissues due to too low temperature on the outer surface of the catheter on the premise of ensuring the cryoablation effect.

SUMMARY

In view of this, an objective of the present application is to provide a cryogenic balloon catheter with a heating function to address the problems in the prior art that when cryogenic fluid is introduced into the balloon catheter, there may have an impact on blood flowing on the outer surface of the catheter, and may even cause the problems that blood vessels are frozen, and human tissues are damaged by freezing.

In order to solve the above technical problems, the present application employs the technical solution as follows.

A cryogenic balloon catheter having a heating function includes a catheter body and an external power source, wherein an outer wall of the catheter body includes an inner layer, a middle layer and an outer layer disposed in sequence from inside to outside, and the middle layer includes a metal woven mesh that is connected in a power supply circuit of the external power source.

Further, the woven metal mesh is a grid-like metal wire woven mesh formed by a plurality of metal wires interwoven with each other.

Further, a temperature controller is arranged in the power supply circuit formed by the external power source and the metal woven mesh.

Further, the outer layer is made of polyether-block-amide resin material.

Further, the inner layer is made of polyether-block-amide resin material.

Further, the temperature controller is electrically connected with a thermocouple embedded in the outer wall of the catheter body.

Further, the thermocouple is embedded in the middle layer of the catheter body.

Further, the metal woven mesh has a proximal end and a distal end, and the positive pole and negative pole of each metal wire in the metal woven mesh are led out from the proximal end.

Further, a conducting ring is disposed at the distal end of the metal woven mesh, and the positive pole and negative pole of each metal wire in the metal woven mesh are connected to the conducting ring at the distal end.

Further, a deflecting guidewire is disposed on an outer side of the outer wall of the catheter body, and the deflecting guidewire, the metal woven mesh and the external power source together form the power supply circuit.

The technical solution of the present application has the following advantages:

1. According to the cryogenic balloon catheter having the heating function provided by the present application, the metal woven mesh having a heat conduction function is arranged in the middle layer of the outer wall of the cryogenic balloon catheter, and is connected with the external power source. The metal woven mesh can generate heat after being powered to ensure that the temperature of the outer surface of the catheter is maintained within the set temperature, thereby not only ensuring the cryoablation effect, and also preventing the problems that cryogenic fluid within the cryogenic balloon catheter transfers cold to the outside of the catheter body to damage the human tissues by freezing.

2. According to the cryogenic balloon catheter having the heating function provided by the present application, the grid-like metal wire woven mesh formed by the plurality of metal wires interwoven with each other generates a large quantity of heat after being powered and can generate heat uniformly throughout the outer wall of the catheter body, which can better ensure that the temperature throughout the outer surface of the catheter body is maintained within the desired temperature range, thereby avoiding the influence on the human tissues outside the catheter body caused by uneven heat generation throughout the catheter body.

3. According to the cryogenic balloon catheter having the heating function provided by the present application, temperature controller is arranged in the power supply circuit formed by the external power source and the metal woven mesh, and the temperature controller can control the heat generation power of the metal woven mesh to better control the temperature of the outer wall of the catheter body to be within the desired temperature range.

4. According to the cryogenic balloon catheter having the heating function provided by the present application, the thermocouple connected with the temperature controller embedded in the middle layer of the catheter body can measure the heat generation temperature of the metal woven mesh at a closer distance more accurately, and feed the measured temperature signals back to the temperature controller. The temperature controller can accurately control the heat generation power of the metal woven mesh more timely, which is in favor of stably maintaining the temperature of the outer wall of the catheter body within the desired temperature range for a long time.

5. According to the cryogenic balloon catheter having the heating function provided by the present application, the positive pole and negative pole of each metal wire in the metal woven mesh are led out from the proximal end, and are connected to the conducting ring at the distal end of the metal woven mesh such that the plurality of metal wires form a parallel circuit, which may increase the generated heat of the metal woven mesh.

6. According to the cryogenic balloon catheter having the heating function provided by the present application, the deflecting guidewire is disposed on the outer wall of the catheter body, and the deflecting guidewire, the metal woven mesh and the external power source together form the power supply circuit, which may take full advantage of the heat generation capability of the metal woven mesh to reduce the heating voltage of the external power source.

BRIEF DESCRIPTION OF THE DRAWINGS

In order to illustrate the specific embodiments of the present application or the technical solution in the prior art more clearly, the drawings required to be used in the description of the specific embodiments or the prior art are simply introduced. Obviously, the drawings in the following description are some embodiments of the present application, and those of ordinary skill in the art may obtain other drawings based on these drawings without creative work.

Figure 1:
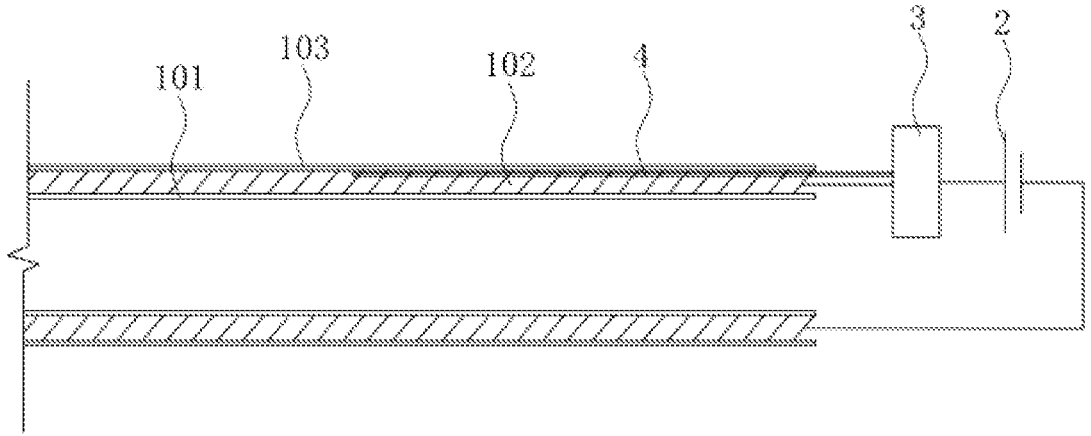
FIG. 1 is a schematic structural diagram showing connection of a cryogenic balloon catheter and an external power source in an embodiment 1 of the present application.

Reference numerals: 101. inner layer; 102. metal woven mesh; 103. outer layer; 104. conducting ring; 2. external power source; 3. temperature controller; 4. thermocouple; 5. deflecting guidewire.

DETAILED DESCRIPTION

The technical solutions of the present application are clearly and completely described below in combination with the drawings. Obviously, the described embodiments are a part of the embodiments of the present application instead of all embodiments of the present application. Based on the embodiments in the present application, all other embodiments acquired by those of ordinary skill in the art without creative work shall fall within the protection scope of the present application.

In the description of the present application, it should be noted that, the orientation or positional relation indicated by terms "center", "upper", "lower", "left", "right", "vertical", "horizontal", "inner", "outer" and the like is based on the orientation or positional relation shown in the drawings. The terms are only for facilitating the description of the present application and simplifying the description, rather than indicating or implying that the device or element referred to must have a specific orientation and be constructed and operated in a specific orientation, and therefore cannot be understood as a limitation to the present application. Further, the terms "first", "second", "third" are only for the descriptive purpose, but cannot understood as indicating or implying relative importance.

In the description of the present application, it should be noted that unless otherwise specified and limited, the terms "mount", "link" and "connect" should be broadly understood, For example, it can be fixed connection, detachable connection or integrated connection; it can be mechanical connection or electrical connection; and it can be direct connection or indirect connection through intermediate media, and may be internal connection of two elements. Those of ordinary skill in the art can understand the specific meanings of the above terms in the present application according to specific situations.

Embodiment 1

Figure 2:
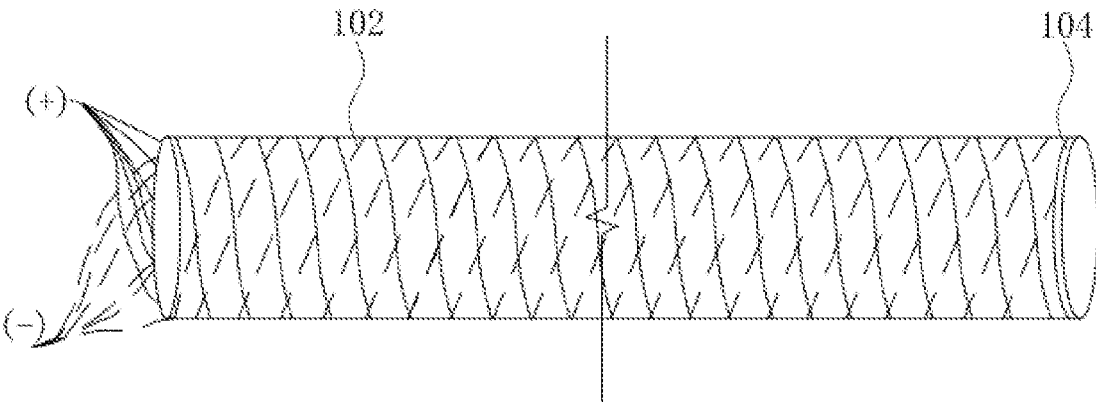
FIG. 2 is a schematic structural diagram of a metal woven mesh in an embodiment of the present application.

As shown in FIGS. 1 and 2, a cryogenic balloon catheter having heating function is used in the field of cryogenic medical devices, wherein the temperature of cryogenic fluid introduced into the cryogenic balloon catheter is generally −80° C. or below. The cryogenic balloon catheter includes a catheter body and an external power source 2. An outer wall of the catheter body includes an inner layer 101, a middle layer and an outer layer 103 disposed in sequence from inside to outside, wherein the inner layer 101 and the outer layer 103 are both made of PEBAX (polyether-block-amide resin) material, and the middle layer is a metal woven mesh 102, the metallic braided mesh 102 that is connected in a power supply circuit of the external power source 2.

In the cryogenic balloon catheter having the heating function, the metal woven mesh 102 having a heat conduction function is arranged in the middle layer of the outer wall of the cryogenic balloon catheter, and is connected in the external power source 2, and the metal woven mesh 102 may generate heat after being powered, which ensures that the temperature of an outer surface of the catheter body is maintained at a set temperature (for example, 10±2° C.), thereby not only ensuring the cryoablation effect, and well addressing a range of problems that when being introduced into the cryogenic balloon catheter, cryogenic fluid transfers cold energy to the outer surface of the cryogenic balloon catheter, resulting in freezing blood vessels outside the cryogenic balloon catheter, damaging the human tissues by freezing, etc.

In this embodiment, a temperature controller 3 is also arranged in the power supply circuit formed by the external power source 2 and the metal woven mesh 102, and the temperature controller 3 is electrically connected with a thermocouple 4 embedded in the middle layer of the catheter body. The thermocouple 4 connected with the temperature controller 3 is embedded in the middle layer of the catheter, which can measure the heat generation temperature of the metal woven mesh 102 at a closer distance more accurately, and feed measured temperature signals back to the temperature controller 3. The temperature controller 3 can accurately control the heat generation power of the metal woven mesh 102 more timely, which is in favor of stably maintaining the temperature of the outer wall of the catheter body within a desired temperature range for a long time.

As shown in FIG. 2, the metal woven mesh 102 is a grid-like metal wire woven mesh formed a plurality of metal wires interwoven with each other by a special weaving process. The metal woven mesh has a proximal end and a distal end, and the positive pole and negative pole of each metal wire in the metal woven mesh are led out from the proximal end. A conducting ring 104 is disposed at the distal end of the metal woven mesh, and the positive pole and negative pole of each metal wire in the metal woven mesh are connected to the conducting ring 104 at the distal end. The plurality of metal wires of the grid-like metal woven mesh form a parallel circuit, and the metal woven mesh generates a large quantity of heat after being powered and can generates heat uniformly throughout the outer wall of the catheter body, which may better ensure that the temperature throughout the outer surface of the catheter body is maintained within the desired temperature range, thereby avoiding the influence on the human tissues outside the catheter body caused by uneven heat generation throughout the catheter body.

Embodiment 2

Figure 3:
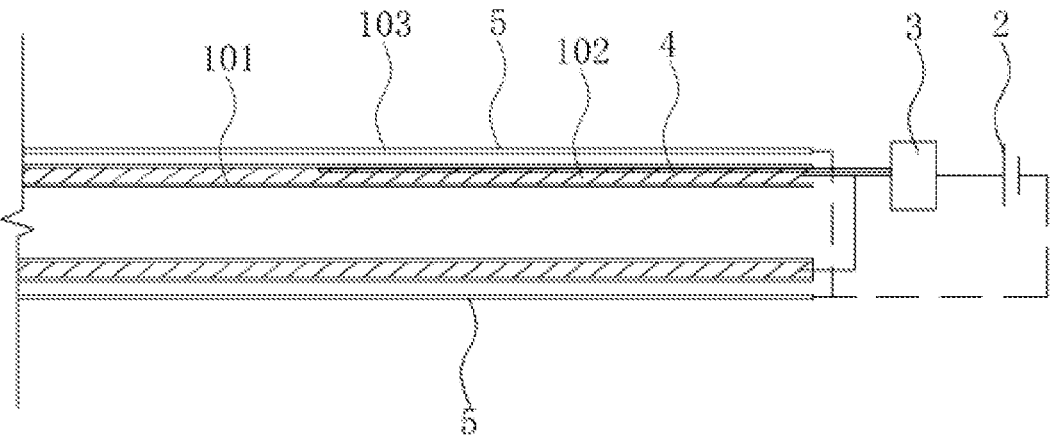
FIG. 3 is a schematic structural diagram showing connection of a cryogenic balloon catheter and an external power source in an embodiment 2 of the present application.

A cryogenic balloon catheter having a heating function as shown in FIG. 3 differs from that in the embodiment 1 in that a deflecting guidewire 5 is disposed on an outer side of the outer wall of the catheter body, and the deflecting guidewire 5, the metal woven mesh 102 and the external power source 2 together form the power supply circuit. The metal woven mesh 102 is connected with the positive pole of the external power source 2, and the deflecting guidewire 5 is connected with the negative pole of the external power source 2. Compared with the solution in the embodiment 1 that the positive pole and negative pole of the metal woven mesh 102 are led out from the same end and are connected with the positive pole and negative pole of the external power source 2 respectively, this solution can take full advantage of the heat generation capability of the metal woven mesh 102 to reduce the heating voltage of the external power source 2.

Obviously, the above embodiments are examples only for clear description, rather than limiting the embodiments. For those of ordinary skill in the art, other different forms of variations or changes can be made on the basis of the above description. It is unnecessary and impossible to enumerate all the embodiments here. The obvious variations or changes derived therefrom are still within the protection scope of the present application.

What is claimed is:

1. A cryogenic balloon catheter having a heating function, comprising:
   a catheter body and an external power source,
   an outer wall of the catheter body comprising an inner layer,
   a middle layer and an outer layer disposed in sequence from inside to outside, and the middle layer comprising a metal woven mesh that is connected in a power supply circuit of the external power source,
   wherein the metal woven mesh is a grid-like metal-wire woven mesh formed by a plurality of metal wires,
   wherein the grid-like metal-wire woven mesh has a proximal end and a distal end, and each metal wire in the grid-like metal-wire woven mesh is led out from the proximal end to be connected to a positive electrode or a negative electrode of the external power source, a conducting ring is disposed at the distal end of the grid-like metal-wire woven mesh, and each metal wire in the grid-like metal-wire woven mesh is connected to the conducting ring at the distal end, such that the plurality of metal wires of the grid-like metal-wire woven mesh form a parallel circuit.

2. The cryogenic balloon catheter having the heating function according to claim 1, wherein a temperature controller is arranged in the power supply circuit formed by the external power source and the metal woven mesh.

3. The cryogenic balloon catheter having the heating function according to claim 1, wherein the outer layer is made of polyether-block-amide resin material.

4. The cryogenic balloon catheter having the heating function according to claim 1, wherein the inner layer is made of polyether-block-amide resin material.

5. The cryogenic balloon catheter having the heating function according to claim 2, wherein the temperature controller is electrically connected with a thermocouple embedded in the outer wall of the catheter body.

6. The cryogenic balloon catheter having the heating function according to claim 5, wherein the thermocouple is embedded in the middle layer of the catheter body.

7. A cryogenic balloon catheter having a heating function comprising:
   a catheter body and an external power source,
   an outer wall of the catheter body comprising an inner layer, a middle layer and an outer layer disposed in sequence from inside to outside, and the middle layer comprising a metal woven mesh that is connected in a power supply circuit of the external power source,
   wherein a deflecting guidewire, i.e., steerable pull wire, is disposed on an outer side of the outer wall of the catheter body, and the deflecting guidewire, the metal woven mesh and the external power source together form the power supply circuit, the deflecting guidewire also has an electrically-conducting function, and within the power supply circuit, the metal woven mesh is connected to a positive electrode of the external power source, and the deflecting guidewire is connected to a negative electrode of the external power source.

8. The cryogenic balloon catheter having the heating function according to claim 7, wherein a temperature controller is arranged in the power supply circuit.

9. The cryogenic balloon catheter having the heating function according to claim 7, wherein the outer layer is made of polyether-block-amide resin material.

10. The cryogenic balloon catheter having the heating function according to claim 7, wherein the inner layer is made of polyether-block-amide resin material.

11. The cryogenic balloon catheter having the heating function according to claim 8, wherein the temperature controller is electrically connected with a thermocouple embedded in the outer wall of the catheter body.

12. The cryogenic balloon catheter having the heating function according to claim 11, wherein the thermocouple is embedded in the middle layer of the catheter body.

* * * * *